(12) United States Patent
Wagner et al.

(10) Patent No.: US 9,204,785 B2
(45) Date of Patent: Dec. 8, 2015

(54) ENDOSCOPE SHEATH, ENDOSCOPE ARRANGEMENT, AND METHOD FOR PROVIDING AN ENDOSCOPE ARRANGEMENT

(71) Applicant: Karl Storz GmbH & Co. KG, Tuttlingen (DE)

(72) Inventors: Sebastian Wagner, Bretten (DE); Bernard Dallemagne, Beauafys (BE); Hyunsoo Chung, Seoul (KR)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 13/922,831

(22) Filed: Jun. 20, 2013

(65) Prior Publication Data

US 2014/0005480 A1    Jan. 2, 2014

(30) Foreign Application Priority Data

Jun. 20, 2012 (DE) .......................... 10 2012 105 370

(51) Int. Cl.
*A61B 1/04* (2006.01)
*A61B 1/00* (2006.01)
*A61B 1/005* (2006.01)
*A61B 17/00* (2006.01)
*A61B 1/018* (2006.01)

(52) U.S. Cl.
CPC ............. *A61B 1/00135* (2013.01); *A61B 1/005* (2013.01); *A61B 1/018* (2013.01); *A61B 17/00234* (2013.01); *A61B 1/00098* (2013.01); *A61B 1/00137* (2013.01)

(58) Field of Classification Search
CPC ........... A61B 1/00098; A61B 1/00135; A61B 1/00137; A61B 1/005; A61B 1/018
USPC .......... 600/104, 121–125, 137, 106, 114, 128
See application file for complete search history.

(56) References Cited

U.S. PATENT DOCUMENTS

| 7,431,694 | B2 * | 10/2008 | Stefanchik et al. ........... 600/104 |
| 7,553,278 | B2 * | 6/2009 | Kucklick ....................... 600/175 |
| 2007/0270646 | A1 | 11/2007 | Weiner | |
| 2008/0188868 | A1 | 8/2008 | Weitzner et al. | |
| 2012/0095291 | A1 | 4/2012 | Nakajima | |
| 2012/0316391 | A1 * | 12/2012 | Weitzner et al. ............. 600/104 |

FOREIGN PATENT DOCUMENTS

DE       60028014 T2    12/2006
DE    102009041510 A1    3/2011

* cited by examiner

*Primary Examiner* — Anhtuan T Nguyen
*Assistant Examiner* — Timothy J Neal
(74) *Attorney, Agent, or Firm* — Whitmyer IP Group LLC

(57) ABSTRACT

An endoscope sheath including an elongate flexible hose, which encloses a main lumen, for receiving at least one portion of a shank of a flexible endoscope, and at least one working channel, for receiving at least one portion of a flexible endoscopic working instrument, wherein the endoscope sheath has a transparent distal end portion. Further provided is an endoscope arrangement, and a method for providing an endoscope arrangement.

1 Claim, 4 Drawing Sheets

ENDOSCOPE SHEATH, ENDOSCOPE ARRANGEMENT, AND METHOD FOR PROVIDING AN ENDOSCOPE ARRANGEMENT

FIELD OF THE INVENTION

The present invention relates to an endoscope sheath, and to an endoscope arrangement and a method for providing an endoscope arrangement.

BACKGROUND OF THE INVENTION

Endoscopic operating techniques have gained widespread use in a large number of surgical procedures. An important advantage of procedures performed by endoscopy is that there is no need for a large incision to be made in the skin and in the underlying tissue in order to gain access to the operating site, and it is thus possible to reduce the burden on the patient and the duration of inpatient treatment. Instead, in endoscopic operations, endoscopes or endoscopic instruments are guided through one or more fairly small incisions or even through a natural access route to the operating site, where the surgical manipulations necessary for performing the procedure can be performed. Particularly if a natural access route is used in order to perform a procedure in a hollow organ or to perform a procedure in the abdomen, for example, through an incision in the wall of the hollow organ, it is advantageous to be able to insert a flexible endoscope through the natural access route together with endoscopic instruments needed to perform the procedure.

Endoscope sheaths have therefore been developed which allow a flexible endoscope to be guided to an operating site together with an endoscopic working instrument.

US 2012/0095291 A1 discloses an endoscope sheath having a first channel for the insertion of an endoscope, wherein a wall enclosing the first channel has a second channel into which an operating instrument can be inserted. The second channel is wound in the form of a helix around the first channel, such that a longitudinal direction of the second channel deviates from a longitudinal direction of the first channel. This has the effect that an endoscopic working instrument guided beyond the distal end of the second channel extends obliquely with respect to the direction of the distal end of an endoscope inserted into the first channel.

According to DE 600 28 014 T2, a controllable endoscope jacket encloses an endoscope, and the jacket also has two lumens that provide channels for the insertion of surgical instruments. To control the deflection of the distal end of the lumens, a wire element is provided that extends along the walls of the lumens and adjacent to the endoscope.

SUMMARY OF THE INVENTION

The object of the present invention is to improve an endoscope sheath of the aforementioned type in terms of its use in endoscopic procedures. This object is achieved by an endoscope sheath including an elongate flexible hose, which encloses a main lumen, for receiving at least one portion of a shank of a flexible endoscope, and at least one working channel, for receiving at least one portion of a flexible endoscopic working instrument, characterized in that the endoscope sheath has a transparent distal end portion, and if appropriate, in an advantageous development, by an endoscope sheath according to the further claims directed to an endoscope sheath.

It is a further object of the present invention to specify an endoscope arrangement which is improved in terms of its use in endoscopic procedures, and to specify a method by which a corresponding endoscope arrangement is provided. This object is achieved by an endoscope arrangement including an endoscope sheath, a flexible endoscope dimensioned for insertion into the main lumen of the endoscope sheath, and a flexible endoscopic working instrument dimensioned for insertion into the working channel of the endoscope sheath, and a method for providing an endoscope arrangement, wherein a flexible endoscope, a flexible endoscopic working instrument and an endoscope sheath are provided, wherein the endoscope sheath includes an elongate flexible hose which encloses a main lumen, for receiving at least one portion of a shank of the flexible endoscope, and at least one working channel, extending parallel to the main lumen and receiving at least one portion of the flexible endoscopic working instrument, and wherein the endoscope sheath has a transparent distal end portion, wherein furthermore at least one portion of the shank of the flexible endoscope is inserted into the main lumen such that a viewing lens of the endoscope is arranged in a distal end area of the endoscope sheath, the distal end area of the endoscope sheath is rotated relative to a proximal end area about a central longitudinal axis of the main lumen, such that the working channel extends helically around the central longitudinal axis of the main lumen, the endoscope sheath is fixed in rotation relative to the endoscope in a proximal and a distal end area, and wherein at least one portion of the flexible endoscopic working instrument is inserted into the working channel.

An endoscope sheath according to the invention comprises an elongate flexible hose, which encloses a main lumen, for receiving at least one portion of a shank of a flexible endoscope, and which is flexible at least in part. The main lumen is designed in particular as a hollow space or channel which is continuous in the longitudinal direction and into which the shank of the flexible endoscope can be inserted, in particular pushed, from a proximal end of the endoscope sheath (i.e. an end near the user) at least to a point near a distal end of the endoscope sheath (i.e. an end remote from the user). In the inserted state, a scene located in front of the distal end of the endoscope sheath can be observed using a viewing lens system arranged at the tip of the endoscope. For this purpose, an image of the scene can be generated for example through an endoscope objective arranged at the tip of the endoscope, which image is recorded by an imager located in the distal end area of the endoscope and is conveyed to the proximal end area of the endoscope through lines extending inside the shank, or which is conveyed by an organized bundle of light-guiding fibers, extending inside the shank, to a camera arranged in the proximal end area of the endoscope. The endoscopic scene, for example an inner wall of a hollow organ, can be illuminated, for example via a light-guiding system arranged inside the shank, with illuminating light generated by a proximally arranged light source. The shank of the endoscope can have a controllable portion, in particular a controllable end portion, which can be actively angled by a certain amount in a desired direction and, for this purpose, can be controlled from the proximal end of the endoscope. For this purpose, control wires, for example, can be provided that extend inside the shank. After at least a portion of the shank of the flexible endoscope has been inserted, a head of the flexible endoscope, which head can have a handle with control elements, connections for supply lines and/or an endoscopic camera, remains outside the endoscope sheath preferably in the area of the proximal end.

The elongate, flexible hose is produced at least in part from a flexible material, for example rubber or a relatively soft plastic. To improve the flexibility, the hose can be designed with a thin wall. The wall thickness can be in the range of 0.3 to 1.5 mm. The hose can be strengthened, for example, by a metal mesh or a wire tube. The endoscope sheath can be provided in particular as a disposable product for single use. Preferably, the endoscope sheath is not designed to be actively controllable, and instead it can be controlled or angled, for example, by a control device of an endoscope inserted into the main lumen of the hose.

The endoscope sheath also has at least one working channel for receiving at least one portion of a flexible endoscopic working instrument. The working channel is designed in particular as a further lumen, or as a hollow space extending continuously from the proximal end area to the distal end area of the hose. Generally, the working channel is designed with a smaller diameter than the main lumen, but with a greater diameter than an endoscope working channel present in a flexible endoscope insertable into the main lumen. In this way, it is possible to use endoscopic instruments of which the diameter is too great to be inserted through such an endoscope working channel. At its distal end, the endoscopic working instrument has a tool which can be controlled from the direction of the proximal end of the shank via transmission means extending inside a shank of the working instrument. The shank of the working instrument is designed to be flexible at least in part. The endoscopic working instrument can be inserted into the working channel at least to the extent that the tool can be used to carry out manipulations in the area of the distal end of the endoscope sheath, in particular in front of the distal end of the endoscope sheath. The working instrument can have a controllable distal end portion, which allows the tool to be angled in order to perform manipulations in a desired direction and at a desired location within the operating site. The working channel is preferably designed in such a way that a controllable distal end portion of the working instrument can be pushed out beyond the distal end of the working channel. Control elements arranged at the proximal end, and used to actuate the tool or to control the distal end portion of the working instrument, can remain outside the proximal end of the endoscope sheath after the endoscopic working instrument has been inserted into the working channel.

According to the invention, the endoscope sheath has a transparent distal end portion. Preferably, the transparent distal end portion takes up only a small part of the total length of the endoscope sheath and is advantageously stiff. In particular, the endoscope sheath can be designed in such a way that a flexible endoscope can be guided with the viewing lens system of the endoscope into or close to the transparent distal end portion, but not to the distal end thereof, which is also the distal end of the endoscope sheath. For this purpose, the main lumen inside the transparent distal end portion can have a step, for example, which prevents further advance of the endoscope, or the length of the endoscope sheath and the length of the endoscope shank can be suitably dimensioned. However, particularly in the case of a lens system providing an oblique view or side view, provision can also be made that the flexible endoscope can be guided as far as the distal end of the endoscope sheath. The transparent distal end portion of the endoscope sheath is designed in particular in such a way that it does not cause trauma.

By virtue of the fact that the endoscope sheath has a transparent distal end portion, it is possible, when inserting the endoscope sheath through an access route to an operating site, to use the viewing lens system of a flexible endoscope inserted into the main lumen to observe a distal edge area of the endoscope sheath and in this way to monitor the insertion of the endoscope sheath. For example, it is thus possible to more reliably ascertain whether a curvature of the endoscope sheath is adapted to a curvature of the access route, or whether, for example, the further insertion of the endoscope sheath is impeded by tissue. In this way, the insertion of the endoscope sheath, provided with a flexible endoscope and with a working instrument, through an access route to an operating site can be simplified and injuries can be avoided. Moreover, by virtue of the fact that a transparent distal end portion is provided, the illumination of the access route or of the cavity within the body can be improved.

According to a preferred embodiment of the invention, the transparent distal end portion is designed to be separable from the hose. For example, the distal end portion can be designed to be releasably connectable to a distal end of the hose by being pushed onto the distal end, clipped on or also screwed on. In this way, the production of the endoscope sheath is simplified. Moreover, the separable design of the distal end portion allows the latter to be replaced during an operation, for example if it has become damaged through contact with a tool of the working instrument.

According to a particularly preferred embodiment of the invention, which is also claimed independently of a transparent design of the distal end portion of the endoscope sheath, the working channel is guided in the form of a helical line around the main lumen, wherein the working channel preferably has a pitch of between 5 and 50 cm with respect to the longitudinal direction of the main lumen. The pitch can be greater at the proximal end than at the distal end. For example, it can be in the range of 30 to 50 cm at the proximal end and between 5 and 10 cm at the distal end. The fact that the working channel is wound helically around the main lumen means that the endoscope sheath is uniformly flexible in all directions. Even when a flexible endoscope is inserted into the main lumen and an endoscopic instrument is inserted into the working channel, it is in this way possible to achieve a uniform flexibility in all directions, without there being a preferential direction. The working instrument inserted into the working channel is then itself wound helically around the endoscope. On account of the slight incline of the working channel relative to the main lumen, the controllability of the working instrument is not substantially restricted by this.

Even when the working channel extends in the form of a helix around the main lumen, the working channel, in the area of the distal end of the endoscope sheath, in particular inside the transparent distal end portion, is preferably directed substantially parallel to the main lumen or to the continuation of the main lumen in the distal end portion. In this way, the controllability of the working instrument is improved when the latter is pushed beyond the distal end of the endoscope sheath.

According to a particularly preferred embodiment of the invention, the distal end of the working channel opens out in an opening arranged obliquely with respect to a longitudinal axis of the main lumen. The opening thus forms an opening plane which is not arranged perpendicularly with respect to the longitudinal axis of the main lumen in the distal end portion of the endoscope sheath. In particular, the opening is laterally offset in relation to a distal opening of the main lumen, which forms the distal end of the endoscope sheath, wherein the opening plane is directed outward at an inclination. The normal of the opening plane thus lies in a plane formed through the central longitudinal axes of the main lumen and of the working channel in a distal end portion of the endoscope sheath, in particular in the transparent distal end portion, but it forms an angle therewith that can be greater than 45°, for example. This not only makes it easier to angle a controllable distal end portion of the working instrument away from the central longitudinal axis of the main lumen, but also creates a design of the distal end portion of the endoscope sheath which is atraumatic, which facilitates the insertion through an access route to the operating site, and which helps avoid injuries.

The distal end of the working channel is preferably designed in such a way that a working instrument pushed beyond the distal end of the working channel is angled outward in relation to the central longitudinal axis of the main lumen in the distal end portion. For this purpose, a ramp or a nose, for example, can be arranged at a distal opening of the working channel, by means of which the flexible endoscopic instrument is angled in an outward direction when guided beyond the distal end of the working channel. In particular, the ramp or nose is arranged on the side of the working channel facing the main lumen, on the inside thereof in the obliquely arranged distal opening of the working channel. The inclination and height of the ramp or nose are advantageously chosen in such a way that the working instrument is angled at such an angle that the tool lies inside the viewing range of the endoscope lens system pushed into the main lumen. In this way, endoscopic manipulations using the tool can be performed under endoscopic visual monitoring, but the tool is arranged far enough outside the center of the field of sight of the endoscope in order not to impede the endoscopic view of the tissue structures relevant to the procedure. In addition, further angling to the outside, or also in the direction of the central longitudinal axis of the main lumen, may be possible by control of a distal end portion of the working instrument.

According to a preferred embodiment of the invention which is also claimed independently of the endoscope sheath having a transparent distal end portion, the hose is divided, in a proximal end area, into at least two sub-hoses, of which the first sub-hose encloses a proximal end area of the main lumen and the second sub-hose encloses a portion of the working channel. At its distal end, the multi-lumen hose thus merges into at least two single-lumen hoses, which can each have a circular cross section. In this way, it is possible to move and to actuate, independently of each other, control elements and connection elements of the flexible endoscope remaining outside the endoscope sheath and to join them without spatial restrictions on corresponding supply devices.

The first and/or second sub-hoses can have a sealing device for sealing the main lumen or the working channel. The sealing device can in particular comprise a valve, such that, even if the working instrument or the endoscope has to be replaced during an operation, the seal remains intact, and an insufflation pressure possibly required for performing the procedure, or an irrigation liquid fed into the operating site, cannot escape through the main lumen or through the working channel. This makes it even easier to perform endoscopic operations.

The endoscope sheath preferably has a plurality of working channels, which can be arranged adjacent to one another, along a circumference of the main lumen, at least in their distal end portion. The plurality of working channels are in particular also arranged adjacent to one another in the transparent distal end portion. The distal end openings of the working channels can be arranged in a common opening plane or can each form their own opening plane. The working channels can be guided, adjacent to one another, helically around the main lumen of the hose. The provision of a plurality of working channels means that it is possible to insert a plurality of working instruments, as a result of which the endoscope sheath can be used for a particularly wide variety of operations. This also applies independently of the endoscope sheath having a transparent distal end portion.

According to a preferred embodiment of the invention which is also claimed independently of the endoscope sheath having a transparent distal end portion, a cross-sectional contour of the hose has a continuous convex curvature or is rectilinear in parts and has a convex curvature in the other parts. The hose is preferably designed with such a cross section in its entire area in which it encloses the main lumen and the at least one working channel. Thus, at least in a partial area, but preferably along its entire length to be inserted into an access route within the body, the hose does not have any areas of concave curvature of its circumference. It is thus ensured that production residues or bodily secretions, which can be removed only with difficulty during cleaning, cannot accumulate in depressions formed by concave areas. Moreover, the convex or at least non-concave curvature of the surface of the hose ensures optimal utilization of an endoscopic access route, for example the esophagus or the urethra.

Preferably, and also independently of the endoscope sheath having a transparent distal end portion, the at least one working channel has an inner lining, which can be designed, for example, as a flexible tube and/or as a coating. The flexible tube can be made, for example, of a stiffer and harder plastics material than the hose, can be strengthened by a helically wound metal wire or a metal mesh, or can be designed as a corrugated hose so as to be able to take up the forces that arise during actuation of the working instrument and to avoid damage to the working channel. The coating, or the material of the tube, can in particular be chosen in such a way that the friction between the outer face of the working instrument and the inner face of the working channel is reduced. This improves the controllability of the working instrument which, during an endoscopic procedure, often has to be rotated and/or pushed to and fro, and it also in particular makes it possible to perform manipulations with tools which require considerable forces to be transmitted for their actuation.

Advantageously, and also independently of the endoscope sheath having a transparent distal end portion, the hose or the endoscope sheath can be formed in one piece or can also be produced as a composite structure. As composite structure, for example, a plurality of single-lumen hoses can be connected to one another, for example adhesively bonded or welded to one another. An inner lining of the working channel can also be designed as a composite structure with the hose. A composite structure of this kind can, for example, be produced by composite extrusion from different materials. This permits particularly simple production of the endoscope sheath.

According to a preferred embodiment, which is also claimed independently of the endoscope sheath having a transparent distal end portion, the endoscope sheath, in particular the hose, has, in a proximal and/or distal end area, fixing means for fixing the endoscope sheath or the hose relative to a flexible endoscope inserted into the main lumen. The proximal fixing means can be assigned in particular to a sub-hose in which the main lumen is guided in the proximal end area of the endoscope sheath. By arranging fixing means at the distal and/or proximal end, it is possible for the endoscope sheath to be held relative to the endoscope shank in a position that is suitable for inserting the endoscope sheath into the access route and for performing the endoscopic procedure. For example, with fixing means arranged at the proximal or distal end, the endoscope can be fixed to the hose in respect of its longitudinal direction. However, particularly in the case of an endoscope providing an oblique view, it is also advantageous if the endoscope shank is fixed in rotation relative to the endoscope sheath. Particularly advantageously, the endoscope sheath can be fixed in rotation relative to the endoscope shank both in its proximal end area and also in its distal end area by respective fixing means. In this way, when an endoscope sheath having a hose with mutually parallel main lumen and working channel is joined together with a flexible endoscope, it is also possible to twist the endoscope sheath in such a way that the working channel is wound helically around the endoscope, and to fix the hose in this position relative to the endoscope. Since the shank of the flexible endoscope is relatively stiff in terms of rotation, an arrangement with a working instrument wound helically around the endoscope can be obtained in which the flexibility is substantially the same in all directions.

The invention further relates to an endoscope arrangement comprising an endoscope sheath as described above, a flexible endoscope suitable for insertion into the main lumen of the endoscope sheath, and at least one working instrument suitable for insertion into the working channel of the endoscope sheath.

The flexible endoscope comprises an elongate shank which is flexible at least in part and which is suitable in particular for insertion into a cavity within the body. In the distal end area of the endoscope shank, a viewing lens system is arranged for viewing an endoscopic scene in the cavity within the body. To record and convey the endoscopic image from the distal end area to the proximal end area of the endoscope, an organized bundle of light-guiding fibers, for example, can be provided extending inside the shank, or an electronic imaging device, for example a CCD chip, which is arranged in the area of the distal end of the shank and of which the signals are transmitted to the proximal end area via electrical lines extending inside the shank. Moreover, a light-guiding system can be arranged inside the shank in order to transport light to the distal end of the endoscope, where it is used to illuminate the cavity. Furthermore, the endoscope shank can contain one or more endoscope working channels for passing endoscopic working instruments from the proximal end area to the distal end area of the shank, with the aid of which working instruments it is possible to perform manipulations within the cavity. The endoscope sheath can in particular be dimensioned and designed in such a way that the flexible endoscope with its viewing lens system can be guided as far as, or to a point close to, a transparent distal end portion of the endoscope sheath, but not as far as the distal end of the endoscope sheath. This facilitates the insertion of the endoscope arrangement and makes it possible in particular with improved endoscopic viewing.

The working instrument comprises a flexible, elongate shank, which is likewise suitable for insertion into a cavity within the body. The working instrument is designed for performing manipulations in the cavity and, for this purpose, has a tool arranged at the distal end of the shank, for example a gripping instrument, formed with two mutually acting jaws, or an HF electrode. The tool can be controlled or powered from the direction of the proximal end of the shank via a transmission means extending inside the shank. A flexible endoscopic working instrument of this kind does not generally have its own lens system for recording an endoscopic image. The diameter of the at least one working channel is in particular greater than a diameter of the endoscope working channel of the endoscope, such that the working instrument can have a shank with a diameter that is not suitable for insertion into a working channel of the endoscope.

The flexible endoscope is preferably controllable at least in a partial area. Alternatively or in addition, the working instrument can also be designed to be controllable at least in a partial area. If the controllable partial area of the endoscope inserted into the endoscope sheath, or of the working instrument inserted into the endoscope sheath, is angled, the endoscope sheath is in this way also angled. Thus, if the flexible endoscope or at least one working instrument is controllable, then the endoscope arrangement, which comprises the endoscope sheath, the flexible endoscope inserted into the latter and the at least one working instrument inserted into the endoscope sheath, is in this way controllable. This facilitates the insertion of the endoscope arrangement through an optionally curved access route to a cavity within the body. Moreover, the endoscope lens system in the cavity can be directed toward a desired partial area or a partial area of the cavity for performing the manipulations. In particular, the at least one working instrument can have a controllable end portion that can be guided beyond a distal end of the working channel in order to be able to perform the manipulations, under endoscopic monitoring, in a desired direction and at a desired location within the cavity.

A method according to the invention for providing an endoscope arrangement comprises the following steps:

- a flexible endoscope and a flexible endoscopic working instrument are provided,
- an endoscope sheath is provided which comprises an elongate flexible hose which encloses a main lumen, for receiving at least one portion of a shank of the flexible endoscope, and at least one working channel, extending parallel to the main lumen and receiving at least one portion of the flexible endoscopic working instrument, wherein the endoscope sheath preferably has a transparent distal end portion,
- at least one portion of the shank of the flexible endoscope is inserted into the main lumen such that a viewing lens of the endoscope is arranged in a distal end area of the endoscope sheath,
- the distal end area of the endoscope sheath is rotated relative to a proximal end area about a central longitudinal axis of the main lumen, such that the working channel extends helically around the central longitudinal axis of the main lumen,
- the endoscope sheath is fixed in rotation relative to the endoscope in a proximal and a distal end area, and
- at least one portion of the flexible endoscopic working instrument is inserted into the working channel.

In this way, an endoscope arrangement can be provided which can be easily inserted through an access route into a cavity within the body in order to perform manipulations using a tool of the working instrument. Moreover, it is possible to use, and if appropriate to replace during the procedure, endoscopic working instruments which, because of their shank diameter, cannot be inserted through working channels of the endoscope. The flexible endoscope is advantageously controllable, in order to be able to control at least a distal end area of the endoscope arrangement for the purpose of facilitating the insertion through the access route and for improving the attainment of an operating field within the cavity.

The step of inserting the endoscopic working instrument into the working channel can also take place before the distal end area is rotated, or even after the endoscope arrangement has been inserted into the cavity within the body. In the former case, the working instrument is advantageously initially inserted only to the extent that a tool of the working instrument does not yet protrude beyond the distal end of the working channel, and it is only after the endoscope arrangement has been inserted into the cavity that the working instrument with the tool is pushed beyond the distal end of the endoscope sheath. A distal end portion of the working instrument is preferably controllable in order to be able to perform manipulations with the tool in a desired direction and at a desired position.

It will be appreciated that the aforementioned features and the features still to be explained below can be used not only in the respectively indicated combination but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which.

DETAILED DESCRIPTION OF THE INVENTION

Figure 1:
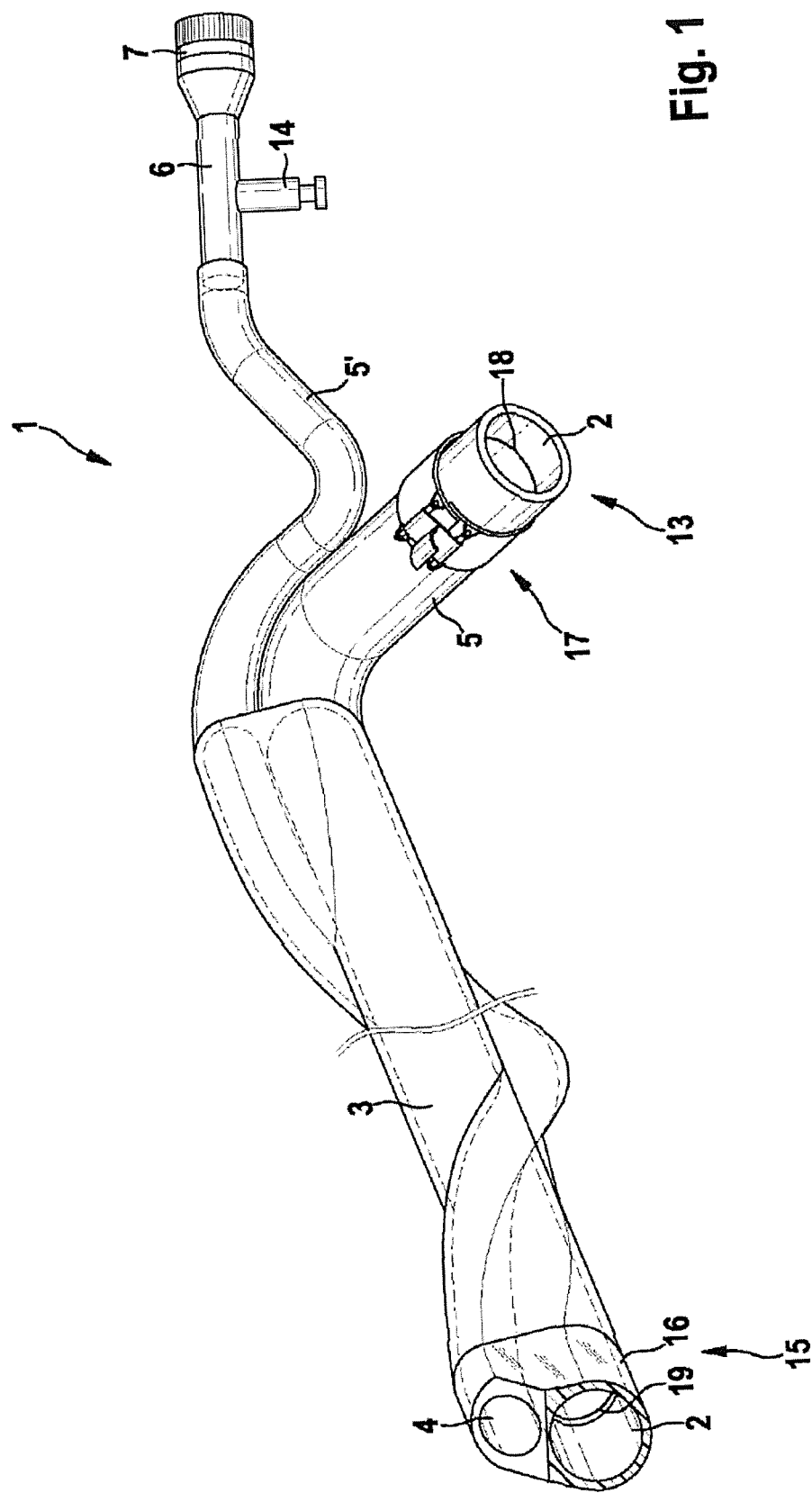
FIG. 1 shows a partially sectioned and perspective view of an illustrative embodiment of an endoscope sheath according to the invention.

As is depicted by way of example in FIG. 1, an endoscope sheath 1 according to the invention comprises a flexible hose 3, which encloses a main lumen 2 extending continuously from a proximal end area 13 to a distal end area 15. The main lumen can, for example, have a circular cross section with an internal diameter of 12.5 mm. The flexible hose 3 also encloses a working channel 4, which likewise extends continuously from the proximal end area 13 to the distal end area 15 and which, for example, can have a circular cross section with an internal diameter of 4.2 mm. The main lumen 2 is designed to receive the shank of a flexible endoscope (not shown), and the working channel 4 is designed to receive the shank of a flexible endoscopic instrument (likewise not shown). In the distal end area 15, a stiff and transparent cap 16 is fitted onto the flexible hose 3, in which cap 16 the main lumen 2 and the working channel 4 are continued as far as the distal end of the endoscope sheath 1 and each open out in distal end openings. The cap can protrude, for example by 5 to 25 mm, beyond the distal end of the hose 3.

The working channel 4 is wound in the form of a helical line or helix around the main lumen 2. The hose 3 is thickened only in that area of its circumference in which the working channel 4 extends, such that the hose 3 is designed with a non-circular, in particular elongate cross section, of which the longitudinal axis rotates about the main lumen 2 as it progresses along the hose 3. The cross section of the hose 3 is partially indicated in FIG. 1, while in the other areas only the main lumen 2 and the working channel 4 are shown, and the hose 3 surrounding both of them is not shown. The angle at which the working channel 4 extends obliquely with respect to the main lumen 2 is exaggerated in FIG. 1. The elongate cross section of the cap 16 is likewise discernible in FIG. 1. The hose 3 can be produced from an elastomer, from PVC, PU, silicone, PTFE, PP, PE or a similar material.

In the proximal end area 13, the hose 3 divides into two sub-hoses 5, 5' which enclose the main lumen 2 and the working channel 4, respectively. The hose 3 can be formed integrally with the sub-hoses 5, 5'. The sub-hose 5' is connected to a rigid guide tube 6, such that the working channel 4 is designed to run continuously through the sub-hose 5' and the guide tube 6 as far as a sealing unit 7 arranged at the proximal end of the guide tube 6. The sealing unit 7 can comprise in particular a sealing lip and a valve, by which the working channel 4 is closed when no working instrument is inserted therein. With a fastening device 14, shown symbolically in FIG. 1, the guide tube 6 can be fastened on a retaining arm (not shown) in order to make the insertion and the control of the working instrument easier.

The sub-hose 5, which encloses a proximal end portion of the main lumen 2, has a fixing device, which is shown symbolically in FIG. 1 as a tightening ring 17 and by means of which the sub-hose 5 and therefore the hose 3 can be fixed on a shank of a flexible endoscope inserted into the main lumen 2. A further fixing device is arranged in the distal end area 15, for example a clamping lip 19 made of rubber, by means of which the hose 3 is fixed, in its distal end area, on the inserted shank of the endoscope. The clamping lip 19 is dimensioned such that the static friction acting on the endoscope shank generally suffices to prevent an axial displacement and a rotation of the hose 3 relative to the inserted endoscope shank during use. By securing the tightening ring 17 after the endoscope shank has been inserted, it is likewise possible to prevent both an axial displacement and also a rotation of the hose 3 relative to the endoscope shank. In this way, it is possible, starting from a hose 3 produced in an untwisted state, i.e. with a substantially rectilinear working channel 4 extending parallel to the main lumen 2, to twist the hose 3 and thereby produce the arrangement shown in FIG. 1 in which the working channel 4 extends helically around the main lumen 2; after the shank of the flexible endoscope is inserted into the main lumen 2, the twisted arrangement can be fixed with the aid of the clamping lip 19 and the tightening ring 17 and secured against untwisting. In this way, an arrangement is obtained with an endoscope sheath which is uniformly flexible in all directions and which is thus optimally adaptable to any curved access routes to an operating site.

Figure 2:
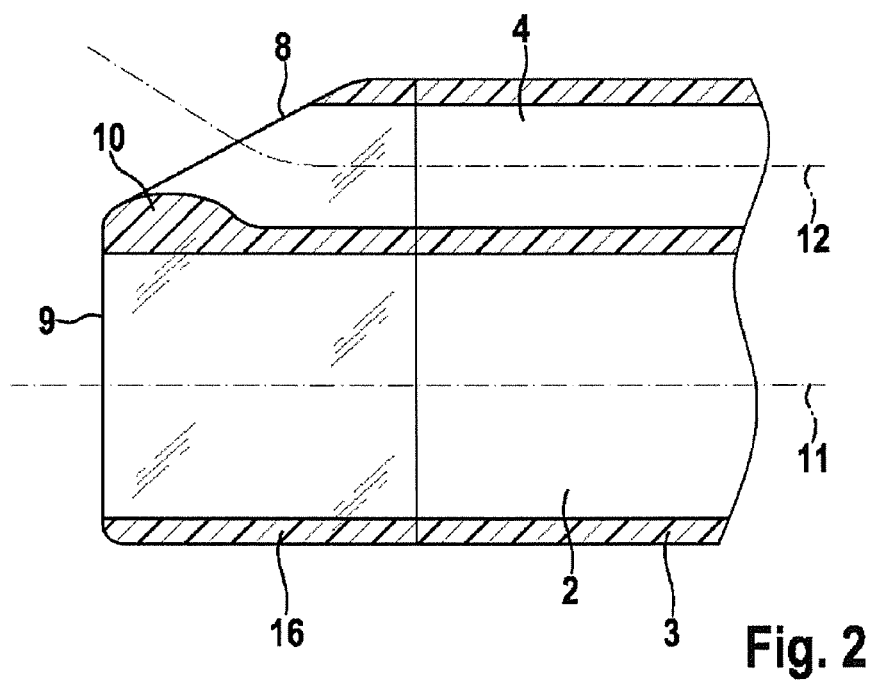
FIG. 2 shows a longitudinal section through the distal end area of the endoscope sheath depicted in FIG. 1.

As is indicated in FIG. 1 and shown in cross section in FIG. 2, the working channel 4, at its distal end in the cap 16, opens out in an end opening 8 arranged obliquely with respect to the longitudinal axis of the distal end portion of the endoscope sheath 1. The longitudinal direction of the endoscope sheath 1 in the distal end portion is given by the central longitudinal axis 11 of the main lumen 2, which opens out in an end opening 9 perpendicular to the central longitudinal axis 11. As is indicated in FIG. 2 by the angling of the distal area of the instrument axis 12 of a flexible endoscopic instrument inserted into the working channel 4, the instrument, when inserted through the opening 8, is deflected by the nose 10, formed as a thickened part of the partition wall between the working channel 4 and the main lumen 2, in a direction away from the main lumen 2. The working channel 4 can continue in the cap 16 in the oblique direction defined by the helical design. However, it is preferably guided in the cap 16 parallel to the central longitudinal axis 11 of the main lumen 2. A working instrument pushed through the working channel 4 and out of the opening 8 is thus oriented in a direction which forms an angle with the central longitudinal axis 11 of the main lumen and preferably extends in a plane formed by the central longitudinal axis 11 and the part of the instrument axis 12 located in the cap 16.

As is indicated in FIG. 2, the distal edges of the cap 16 are rounded in order to facilitate the insertion of the endoscope sheath into a cavity within the body and to avoid injuries in the access route. For the same reason, the cap 16 can be made from a particularly soft material.

Figure 3:
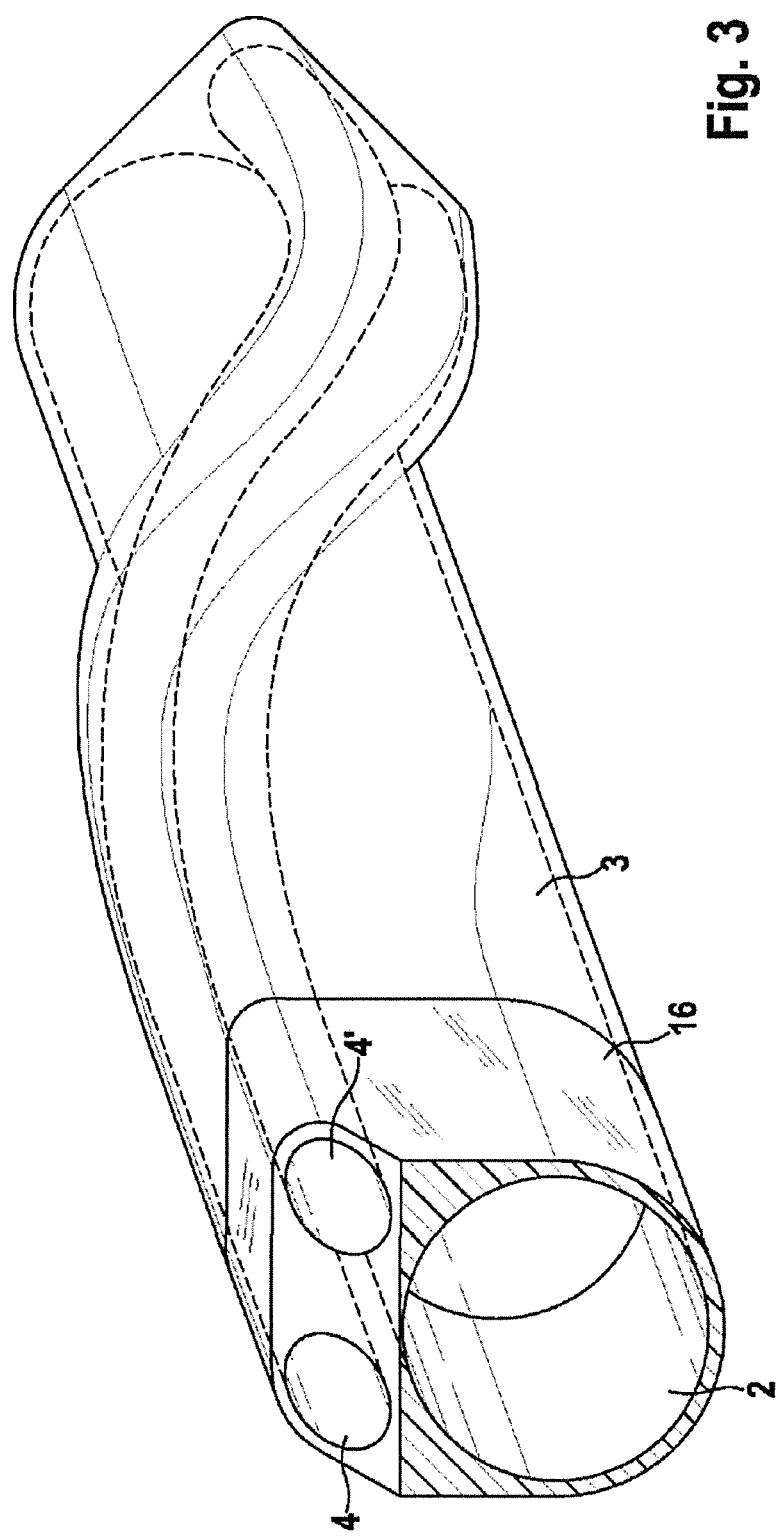
FIG. 3 shows a partially sectioned and perspective view of the distal end area of an endoscope sheath according to a further illustrative embodiment of the invention.

According to a further illustrative embodiment, of which the distal end area is depicted in FIG. 3, the hose 3 and the cap 16 can have a plurality of working channels 4, 4', which in particular are arranged adjacent to one another along a circumference of the main lumen 2, are substantially parallel to one another and, similarly to what is described for FIG. 1, extend in a helical shape around the main lumen 2. In this way, it is possible to insert several working instruments, which can cooperate with one another, through the working channels 4, 4' and to use these to perform manipulations under endoscopic monitoring. In other respects, the illustrative embodiment shown in FIG. 3 is designed like the one in FIGS. 1 and 2, wherein an endoscope sheath of this kind can have, in its proximal end area (not shown), a dedicated sub-hose for each of the working channels 4, 4', each sub-hose having its own guide tube and its own sealing unit.

Figure 4:
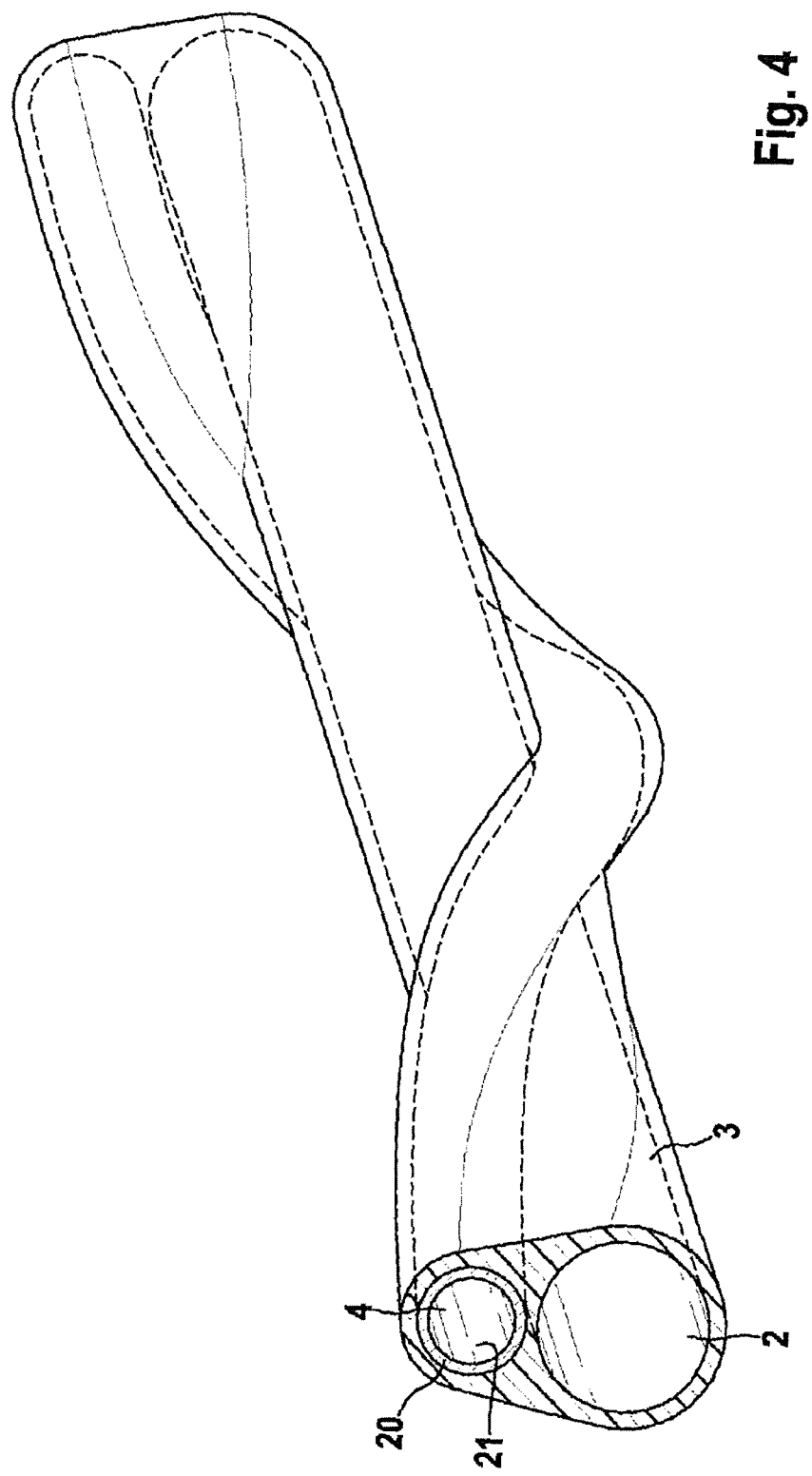
FIG. 4 shows a partially sectioned view of the hose of an endoscope sheath according to one illustrative embodiment of the invention.

As is shown in FIG. 4, the working channel 4, at least inside the hose 3, can have an inner tube 20 that can be made stiffer compared to the material of the hose 3. The inner tube can be strengthened, for example, by a helically wound wire or by a wire mesh or can be produced from a stiffer plastic. This permits improved guiding of the working instrument even when a force is exerted, as may be necessary when performing the endoscopic manipulations. A friction-reducing coating 21 can be arranged on the inside face of the inner tube in order to improve the mobility of the working instrument inside the working channel 4. The design of the working channel 4 depicted in FIG. 4 can be realized in the illustrative embodiment shown in FIG. 1 and, and likewise for the plurality of working channels 4, 4' in the illustrative embodiment shown in FIG. 3.

In order to provide an endoscope arrangement suitable for performing an endoscopic procedure, the following are initially made available: a flexible endoscope with a lighting and viewing lens system suitable for the planned endoscopic procedure and optionally with suction and irrigation channels, a flexible endoscopic working instrument suitable for performing the manipulations planned for the procedure, and an endoscope sheath 1 designed according to FIG. 1, for example, and with a hose 3. The endoscope can be a standard gastroscope, for example, and the working instrument can be a controllable endoscopic instrument intended for use in gastroscopy. The endoscope sheath 1 is dimensioned to receive at least one portion of the shank of the flexible endoscope and to receive at least one portion of the flexible endoscopic working instrument. The working channel 4 of the endoscope sheath 1 extends substantially parallel to the main lumen 2 provided for receiving the endoscope shank.

A portion of the shank of the endoscope is now pushed into the main lumen 2 of the hose 3 of the endoscope sheath 1 until the viewing lens system of the endoscope is arranged substantially at the distal end of the hose 3 or protrudes slightly beyond this. A stiff, transparent cap 16 is fitted onto the distal end of the hose 3. The viewing lens system of the endoscope is then arranged in such a way as to permit viewing of an endoscopy scene located in front of the distal end of the endoscope sheath 1, i.e. in front of the cap 16. For this purpose, the endoscope lens system can be designed, for example, as a straight-view lens system, in which case the endoscopic image recorded via an endoscope objective is conveyed by an image carrier to a camera arranged in the handle of the endoscope. The image recorded by the camera can be presented on a screen for viewing by a user.

The distal end area of the endoscope sheath 1 or of the hose 3 is then rotated about a central longitudinal axis 11 of the main lumen 2 relative to a proximal end area of the hose 3 in a substantially rectilinear state of the hose 3, such that the working channel 4 extends helically around the central longitudinal axis 11 of the main lumen 2. In its distal end area, the hose 3 of the endoscope sheath is rotationally fixed relative to the endoscope via the clamping lip 18. In the proximal end area, the sub-hose 5 of the hose 3 is clamped on the shank of the flexible endoscope with the aid of a tightening ring 18. The helically rotated arrangement of the hose 3 is thus fixed the torsional stiffness of the endoscope shank.

Now, or even at an earlier stage, the flexible endoscopic working instrument is also inserted into the working channel 4, which has a greater diameter than, for example, a working channel of a gastroscope and thus permits the use of working instruments of larger shank diameter. The working instrument is initially advanced in the distal direction only to the extent that the tool does not yet protrude beyond the distal end opening 8 in the cap 16. It is also possible to insert the working instrument into the working channel 4 only after the endoscope arrangement has been inserted into the cavity within the body, or to withdraw this working instrument during the procedure and replace it with another one.

In order to carry out the planned procedure, the endoscope arrangement, composed of the endoscope sheath and of the endoscope and if appropriate of the working instrument, is inserted through an access route into a cavity within the body. The access route can be the esophagus, for example, if a procedure is to be performed inside the stomach, for example an endoscopic sampling procedure, of if, for example, an access route has to be opened up through the hollow organ in order to perform an operation in the abdominal cavity. The endoscope arrangement can be controlled by a control device of the endoscope, thus making the insertion easier and allowing the distal end of the endoscope arrangement to be aligned with an operating site inside the cavity. During the insertion through the access route, the cap 16 keeps the tissue at a distance from the distal end of the endoscope, such that an edge of the cap 16 remains visible during insertion and reliable endoscopic monitoring of the insertion procedure is possible. The endoscopic instrument is also visible inside the part of the working channel 4 extending in the cap 16.

After the operating site has been reached, the working instrument is advanced such that the tool is pushed out through the opening 8 beyond the distal end of the endoscope sheath. The nose 10 causes a deflection of the distal end portion of the working instrument, such that the latter remains within the range of sight of the viewing lens system but is arranged outside the image center. By controlling the distal end portion of the working instrument, the tool can be moved while the position and orientation of the endoscope remain unchanged. Moreover, the distal end of the endoscope arrangement with the endoscope and with the working instrument can be turned by rotating the proximal end of the endoscope. In this way, a wide variety of endoscopic procedures can be performed with optimal monitoring.

For the sake of clarity, not all the reference signs are shown in all of the figures. Reference signs not explained in connection with one figure have the same meaning as in the other figures.

LIST OF REFERENCE SIGNS 1 endoscope sheath
2 main lumen
3 hose
4, 4' working channel
5, 5' sub-hose
6 guide tube
7 sealing unit
8 end opening
9 end opening
10 nose
11 central longitudinal axis
12 instrument axis
13 proximal end area
14 fastening device
15 distal end area
16 cap
17 tightening ring
18 sealing lip
19 clamping lip
20 inner tube
21 coating

The invention claimed is:

1. A method for providing an endoscope arrangement, wherein a flexible endoscope, a flexible endoscopic working instrument and an endoscope sheath are provided, wherein the endoscope sheath comprises an elongate flexible hose which encloses a main lumen, for receiving at least one portion of a shank of the flexible endoscope, and at least one working channel, extending parallel to the main lumen and receiving at least one portion of the flexible endoscopic working instrument, and wherein the endoscope sheath has a transparent distal end portion, wherein furthermore at least one portion of the shank of the flexible endoscope is inserted into the main lumen such that a viewing lens of the endoscope is arranged in a distal end area of the endoscope sheath, the distal end area of the endoscope sheath is rotated relative to a proximal end area about a central longitudinal axis of the main lumen, such that the working channel extends helically around the central longitudinal axis of the main lumen, the endoscope sheath is fixed in rotation relative to the endoscope in a proximal and a distal end area, and wherein at least one portion of the flexible endoscopic working instrument is inserted into the working channel.

* * * * *